(12) United States Patent
Reitan et al.

(10) Patent No.: US 7,955,386 B2
(45) Date of Patent: *Jun. 7, 2011

(54) MIDDLE EAR PROSTHESIS

(75) Inventors: Harlan J. Reitan, Memphis, TN (US); Michael D. White, Olive Branch, MS (US); Anthony D. Prescott, Arlington, TN (US); J. Patrick Ireland, Cordova, TN (US); Casper Briggs, Arlington, TN (US); Robert Brosnahan, Germantown, TN (US)

(73) Assignee: Clarity Corporation, Memphis, TN (US)

( * ) Notice: Subject to any disclaimer, the term of this patent is extended or adjusted under 35 U.S.C. 154(b) by 389 days.

This patent is subject to a terminal disclaimer.

(21) Appl. No.: 11/789,629

(22) Filed: Apr. 25, 2007

(65) Prior Publication Data

US 2007/0255405 A1   Nov. 1, 2007

Related U.S. Application Data

(63) Continuation-in-part of application No. 10/976,638, filed on Oct. 29, 2004, now Pat. No. 7,288,113, and a continuation-in-part of application No. 11/428,672, filed on Jul. 5, 2006, which is a continuation of application No. 10/666,451, filed on Sep. 19, 2003, now Pat. No. 7,087,081.

(60) Provisional application No. 60/823,914, filed on Aug. 30, 2006, provisional application No. 60/853,938, filed on Oct. 24, 2006.

(51) Int. Cl.
*A61F 2/18* (2006.01)

(52) U.S. Cl. ....................................................... 623/10
(58) Field of Classification Search .................... 623/10, 623/11.11, 16.11; 606/151, 154, 155, 259–261, 606/276–278, 300, 323, 324, 326–328; 403/205
See application file for complete search history.

(56) References Cited

U.S. PATENT DOCUMENTS

| | | | |
|---|---|---|---|
| 3,722,003 | A | 3/1973 | Walchle |
| 3,913,444 | A | 10/1975 | Otte |
| 3,931,648 | A | 1/1976 | Shea, Jr. |
| 3,939,828 | A | 2/1976 | Mohr et al. |
| 4,170,990 | A | 10/1979 | Baumgart et al. |
| 4,233,690 | A | 11/1980 | Akins |
| 4,624,672 | A * | 11/1986 | Lenkauskas ............ 623/10 |
| 4,665,906 | A | 5/1987 | Jervis |
| 5,306,299 | A | 4/1994 | Applebaum |
| 5,514,177 | A | 5/1996 | Kurz et al. |
| 5,876,434 | A | 3/1999 | Flomenblit et al. |
| 6,095,713 | A * | 8/2000 | Doyle et al. ............. 403/97 |
| 6,168,625 | B1 | 1/2001 | Prescott |
| 6,197,060 | B1 | 3/2001 | Knox |
| 6,554,861 | B2 | 4/2003 | Knox et al. |
| 6,726,719 | B2 | 4/2004 | Antonelli et al. |

(Continued)

FOREIGN PATENT DOCUMENTS

EP   998884 A2 *  5/2000

(Continued)

*Primary Examiner* — Suzette J Gherbi
(74) *Attorney, Agent, or Firm* — Wood, Phillips, Katz, Clark & Mortimer (57) ABSTRACT

A middle ear prosthesis comprises a body of deformable material capable of retaining different shapes. The body comprises a slotted wall defining a cavity for receiving a bone of the middle ear. The wall is deformable proximate slots in the wall between an open position for receiving the bone and a closed position wherein the body is reshaped to grasp the bone.

21 Claims, 5 Drawing Sheets

U.S. PATENT DOCUMENTS

| | | |
|---|---|---|
| 7,087,081 B2 | 8/2006 | Prescott et al. |
| 7,288,113 B2 * | 10/2007 | Reitan et al. .................... 623/10 |
| 2002/0045939 A1 * | 4/2002 | Kurz .............................. 623/10 |
| 2003/0097178 A1 * | 5/2003 | Roberson et al. ............... 623/10 |

FOREIGN PATENT DOCUMENTS

| | | |
|---|---|---|
| EP | 1 438 931 A1 | 7/2004 |
| EP | 1 759 662 A | 3/2007 |
| WO | WO98/16175 A | 4/1998 |

* cited by examiner

MIDDLE EAR PROSTHESIS

CROSS REFERENCE

This application is a continuation-in-part of Ser. No. 10/976,638, filed Oct. 29, 2004 now U.S. Pat. No. 7,288,113, and a continuation-in-part of Ser. No. 11/428,672, filed Jul. 5, 2006, which is a continuation of U.S. Ser. No. 10/666,451, filed Sep. 19, 2003, now issued as U.S. Pat. No. 7,087,081, and claims benefit of both Ser. Nos. 60/823,914, filed Aug. 30, 2006, and 60/853,938, filed Oct. 24, 2006.

FIELD OF THE INVENTION

This invention relates to an ossicular prosthesis used for replacement and reconstruction and, more particularly, to a middle ear prosthesis of a deformable material.

BACKGROUND OF THE INVENTION

Due to disease, trauma, or congenital malformation, the ossicles of the middle ear are sometimes damaged. The delicate joint between the incus and the stapes is termed the incudo-stapedial joint (ISJ). The ISJ is a cartilaginous joint having a tendency to ossify in older humans. When the joint is interrupted due to erosion of the joint or the incus itself, vibrations can no longer be transmitted from the incus to the stapes. The result is a conductive hearing loss related to the disrupted ossicular chain.

Medical implants have been developed to reconstruct the ossicular chain when a portion of the incus is missing. However, the entire incus has to be removed and replaced with a prosthesis. This approach destroys the natural joint between the incus and stapes and the lever function of the incus in relationship to the malleus and stapes.

One particular implant to address conditions when only the ISJ is eroded or ossified is shown in U.S. Pat. No. 5,306,299. This prosthesis is made from a hydroxylapatite. Particularly, the prosthesis comprises a block of hydroxylapatite having a cylindrical cavity intersecting with a U-shaped channel. The prosthesis cannot be adjusted to conform to various sized incus and stapes. As such, the prosthesis must be provided in different sizes for different size ossicular chains. Because of its mass and lack of features to stabilize its connection to the incus and stapes, it is possible for the prosthesis to migrate and extrude through the ear drum over a period of time. Concerns over the weight of the ceramic material and the overall mass of the prosthesis have been raised. Also, the hydroxylapatite material is inherently fragile, prone to breakage and cannot be easily modified to custom fit the incus or stapes head.

An alternative ISJ prosthesis is disclosed in U.S. Pat. No. 5,514,177. This prosthesis is formed of composite construction using pieces of different materials secured together such as by welding.

Certain ossicular prosthetics require that they be manually crimped to the bone. Fixating or crimping an ossicular prosthesis to bone can be difficult due to problems with prosthesis stability, surgical exposure, appropriate clamping, etc. It is desirable to have a prosthesis that is "self-crimping". Ideally, the self crimping prosthesis should be low profile and provide secure, stable fixation. It should also be easy to apply without damaging the ossicles and apply a small amount of pressure to the ossicles so as to minimize the potential for pressure necrosis.

U.S. Pat. Nos. 6,197,060 and 6,554,861 describe various ossicular prostheses that include a shape memory wire or ribbon reversely turned on itself to form an open-ended bight. The bight is opened with a tool and then automatically closed and crimped about an ossicle upon the application of a signal such as heat. However, such a bight structure is ineffective for coupling various ossicular bones together, either because of the anatomy or because of the lack of the stability provided.

The present invention is directed to improvements in middle ear prosthetics.

SUMMARY OF THE INVENTION

In accordance with one aspect of the invention, there is provided an adjustable middle ear prosthesis.

Broadly, there is disclosed in accordance with one aspect of the invention, an adjustable middle ear prosthesis comprising a unitary body of deformable material capable of retaining different shapes. The body can be reshaped to fit to and retain ossicular bones, such as the stapes and the incus, in a desired relationship. The body is preferably made of a malleable titanium, such as soft unalloyed titanium, or a shape memory material such as nickel-titanium or a polymer.

In one embodiment of the invention, the body comprises a generally tubular first cavity for receiving a head of a stapes and an elongate second cavity extending generally perpendicular to the generally tubular first cavity for receiving an incus. The body comprises a collar defining the generally tubular first cavity. The collar may have a longitudinally extending through slot, and may include a pair of opposite longitudinally extending through slots. The body comprises a generally semi-cylindrical wall connected to opposite parallel walls having inwardly extending flanges defining the elongate second cavity. The semi-cylindrical wall may include a keyhole slot. The opposite parallel walls may be connected to the semi-cylindrical wall by bridges to define elongate slots between the opposite parallel walls and the semi-cylindrical wall. The flanges are spaced apart to define a cavity slot. The opposite parallel walls with flanges extending inward therefrom together define a generally U-shaped wall. The U-shaped wall and semi-cylindrical wall together define the second cavity extending generally perpendicular to the first cavity for receiving an incus.

According to a second embodiment of the invention, an ISJ prosthesis is provided including first and second slotted tubular portions perpendicularly arranged relative to each other. The first slotted tubular portion includes one or more wall portions that are opened and the second slotted tubular portion includes fingers that are opened. The wall portions and fingers are deformed about the stapes and incus, preferably by the application of heat, to stably hold the stapes and incus in the desired anatomical relationship.

According to third embodiment of the invention, an angular piston prosthesis is provided in which a slotted tubular portion is provided on a rod element. The slotted tubular portion includes one or more arms that can be deformed about the incus, such as by application of heat, and the rod element is sized in length to extend from the incus to the stapes footplate or oval window.

According to a fourth embodiment of the invention, a partial ossicular replacement prosthesis (PORP) is provided. The prostheses includes an inverted cup defining a cavity for the head of the stapes, a shaft extending from the cup, and a disc at the end of the shaft for placement against the tympanic membrane. The disc may be longitudinally displaceable on the shaft to adjust the length of the prosthesis. According to the invention, the cup includes at least one slot defined in a wall thereof permitting the circumference of the wall to be deformed into an open position to facilitate receiving the head of the stapes and then closed upon application of heat to retain the stapes.

According to a fifth embodiment of the invention, another PORP is provided including a shaft, a disc at one end, and a mount for engaging the head or capitulum of the stapes at the other end. The mount includes two side walls each provided with a longitudinal recess in which to receive the arch of the stapes. Between the side walls an anchor tab is provided and has a length sufficient to extend across the diameter of the mount. The tab is deformed open to permit the arch of the stapes access into the recesses. Then, upon application of heat to the tab, the tab automatically deforms to bend through the arch and under the capitulum to lock the stapes to the PORP.

Further features and advantages of the invention will be readily apparent from the specification and from the drawings.

DETAILED DESCRIPTION OF THE INVENTION

Figures 1, 2:
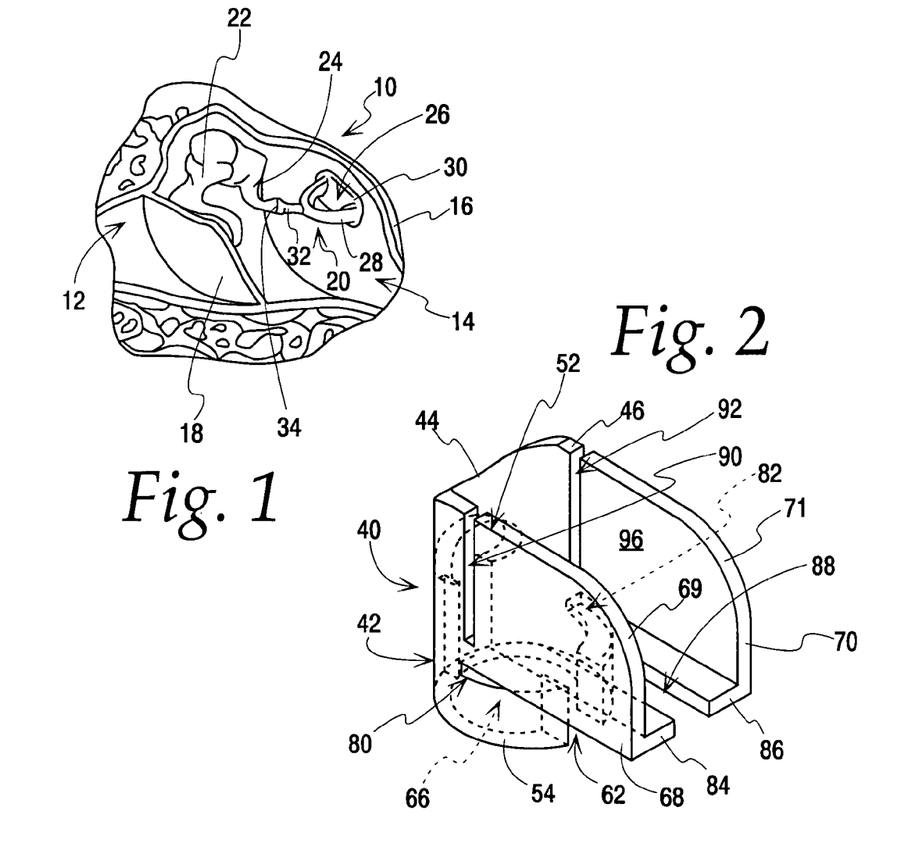
FIG. 1 is a perspective, partial cross-section of the anatomy of an ear showing a normal ossicular chain.
FIG. 2 is a perspective view of an adjustable incudo-stapedial joint (ISJ) prosthesis in accordance with the invention.
Figure 3:
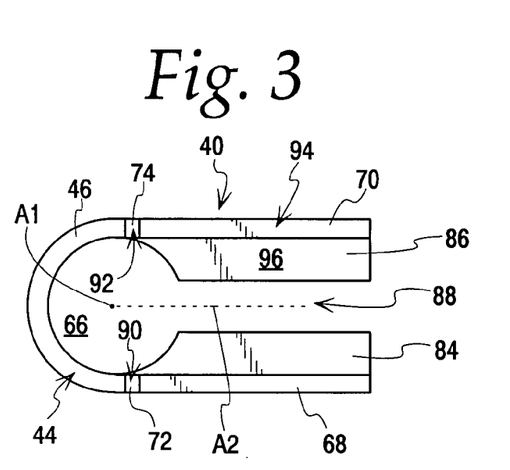
FIG. 3 is a top plan view of the ISJ prosthesis of FIG. 2.
Figure 4:
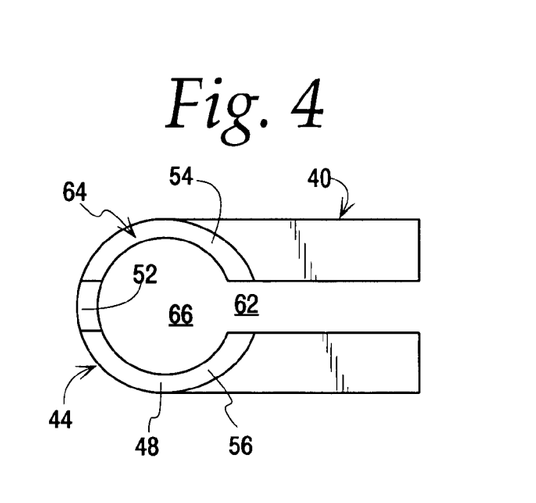
FIG. 4 is a bottom plan view of the ISJ prosthesis of FIG. 2.
Figure 5:
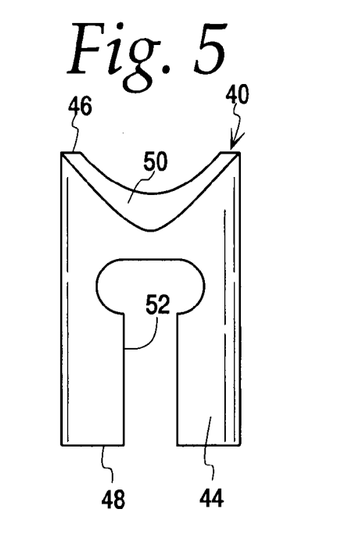
FIG. 5 is a front elevation view of the ISJ prosthesis of FIG. 2.
Figure 6:
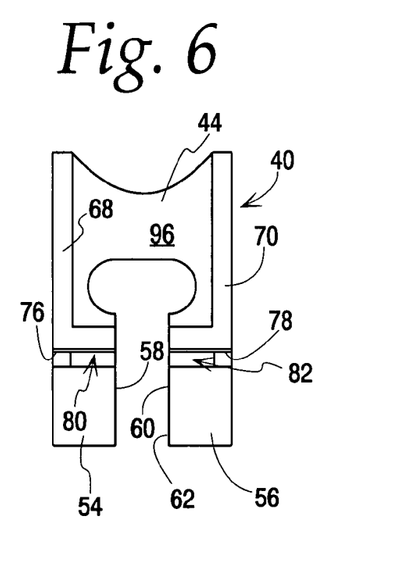
FIG. 6 is a rear elevation view of the ISJ prosthesis of FIG. 2.
Figure 7:
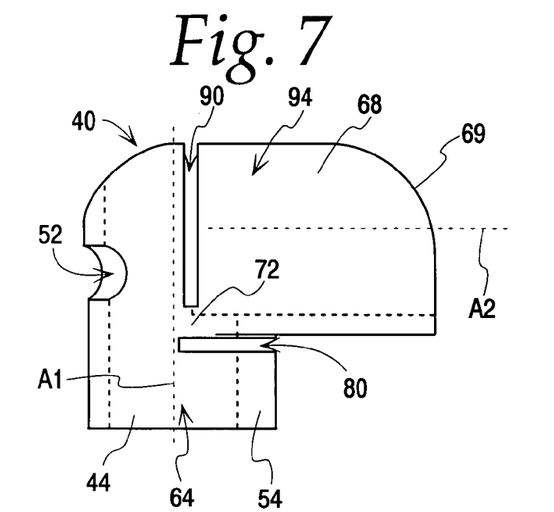
FIG. 7 is a side elevation view of the ISJ prosthesis of FIG. 2.

Referring initially to FIG. 1, a human ear 10 includes an external or outer ear 12, a middle ear 14 and an inner ear 16. A tympanic membrane 18, also called the ear drum, separates the outer ear 12 from the middle ear 14. The middle ear 14 includes an ossicular chain 20 comprising three small bones that are connected and transmit the sound waves from the ear drum 18 to the inner ear 16. The three small bones are called the malleus 22, the incus 24, and the stapes 26. The stapes 26 includes a loop or arch 28 connected to a footplate 30. A head (capitulum) 32 at the top of the arch 28 connects to the lenticular process of the incus 24 at an incudo-stapedial joint (ISJ) 34.

In accordance with the invention, an ISJ prosthesis 40, see FIGS. 2-7, is used when only the ISJ and possibly a short segment of the distal aspect of the long arm of the incus is eroded or ossified. In accordance with this disclosed aspect of the invention, the ISJ prosthesis 40 contains a series of slots enabling the prosthesis to be adjusted in multiple planes to provide a custom fit to either the incus 24 or the stapes head 32.

The ISJ prosthesis 40 is of unitary construction manufactured, such as by machining, to form a one-piece deformable, malleable metal body 42. For ease of description herein, the body 42 is described referring to the left-most part in FIGS. 3 and 4 as the front and the right-most part in FIGS. 3 and 4 as the rear. It should be understood, however, that these relative terms are for reference only in describing the device and do not describe any particular characteristics of the prosthesis 40.

The body 42 comprises a generally semi-cylindrical wall 44 having a top end 46 and a bottom end 48. A rounded notch 50 is provided proximate the top end 46. A keyhole slot 52 is provided through the semi-cylindrical wall 44 originating at the bottom end 48.

The semi-cylindrical wall 44 is connected to opposite arcuate wall portions 54 and 56 at its bottom end 48. The arcuate wall portions 54 and 56 have respective distal edges 58 and 60 spaced apart to define a collar slot 62. The semi-cylindrical wall bottom end 48 and the arcuate wall portions 54 and 56 form a bottom tubular wall 64 slotted with the keyhole slot 52 and the collar slot 62. The slotted tubular wall 64 defines a generally tubular cavity 66 extending along a first axis A1. The tubular cavity 66 is adapted for receiving the head 32 of the stapes 26 during implantation.

Opposite parallel walls 68 and 70 extend tangentially from the semi-cylindrical wall 44 and are connected thereto by respective bridges 72 and 74. Top rear corners 69 and 71 are rounded. The walls 68 and 70 have respective lower edges 76 and 78 spaced above the respective arcuate wall portions 54 and 56 to define spacer slots 80 and 82. The opposite parallel walls 68 and 70 have inwardly extending, spaced apart flanges 84 and 86 to define an elongate slot 88 therebetween. The opposite parallel walls 68 and 70 are spaced from the semi-cylindrical wall 44 above the respective bridges 72 and 74 to define respective front slots 90 and 92.

The semi-cylindrical wall 44 at the top end 46 and the side walls 68 and 70 form a generally U-shaped wall 94 defining an elongate cavity 96 extending along a second axis A2 substantially perpendicular to an axis A1 for receiving an incus 24. As is apparent, the elongate cavity 96 is open from the top or rear for receiving an incus 24 with the incus 24 resting on the flanges 84 and 86. As is apparent, the orientation of the elongate cavity 96 is generally perpendicular to the tubular cavity 66 owing to the conventional relationship in orientation between the incus 24 and stapes head 32.

In accordance with the invention, the body 42 is of one piece construction of a deformable or crimpable (i.e., malleable) metal capable of retaining different shapes. In one exemplary embodiment of the invention, the ISJ prosthesis 40 is formed of an unalloyed titanium for surgical implant applications. For example, the prosthesis 40 may be made of a titanium that satisfies the specifications of AFTM standard F67. This standard identifies four grades of unalloyed titanium for surgical implant applications. The grades are numbered 1, 2, 3 and 4. The grades range from 1 which is a relatively soft titanium that is readily malleable to grade 4 which is relatively hard and more spring-like. Advantageously, the prosthesis 40 is made of a grade 2 titanium to be malleable. As is apparent, it could be made of other grades, most particularly grades 1 or 3 according to an amount of malleability desired. Moreover, as discussed further below, the prosthesis 40 can be manufactured from a shape memory material. The mass and weight of the prosthesis 40 is greatly reduced when compared to ceramic ISJ prostheses. The rounded geometry allows reconnection of the ISJ without introducing sharp edge interference for surrounding structures and bone.

In an exemplary embodiment to the invention, the prosthesis 40 has a front to rear dimension of about 2.5 mm and a height of about 2.0 mm, and a width of about 1.27 mm. The tubular cavity 66 may have a radius on the order of 0.5 mm. The elongate cavity 96 may have a height of about 1.27 mm, width of about 1.0 mm and length, not including the space above the tubular cavity 66 of about 1.5 mm. The wall thickness is generally uniform and may be on the order of 0.1 mm. The prosthesis 40 may be formed by machining or the like. As is apparent, the dimensions of the prosthesis 40 could be different from that described herein according to the needs within the medical community.

Figure 8:
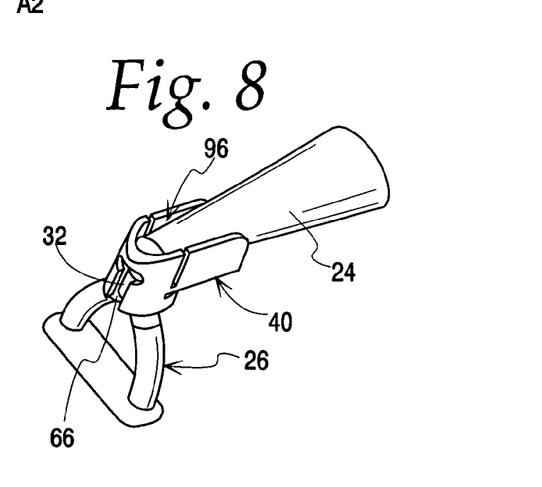
FIG. 8 is a perspective view illustrating the ISJ prosthesis in accordance with the invention implanted in a human ear.
Figures 9, 10, 11, 12:
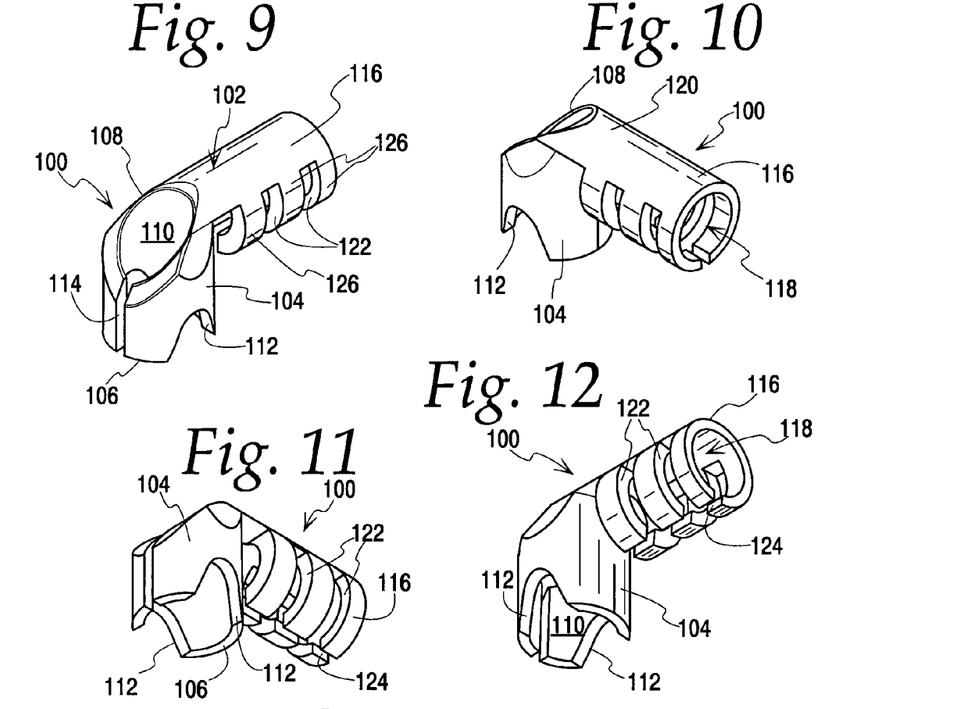
FIG. 9 is an upper front perspective view of an ISJ prosthesis in accordance with an alternative embodiment of the invention.
FIG. 10 is an upper rear perspective view of the ISJ prosthesis of FIG. 9.
FIG. 11 is a lower front perspective view of the ISJ prosthesis of FIG. 9.
FIG. 12 is a lower rear perspective view of the ISJ prosthesis of FIG. 9.
Figures 13, 14, 15, 16:
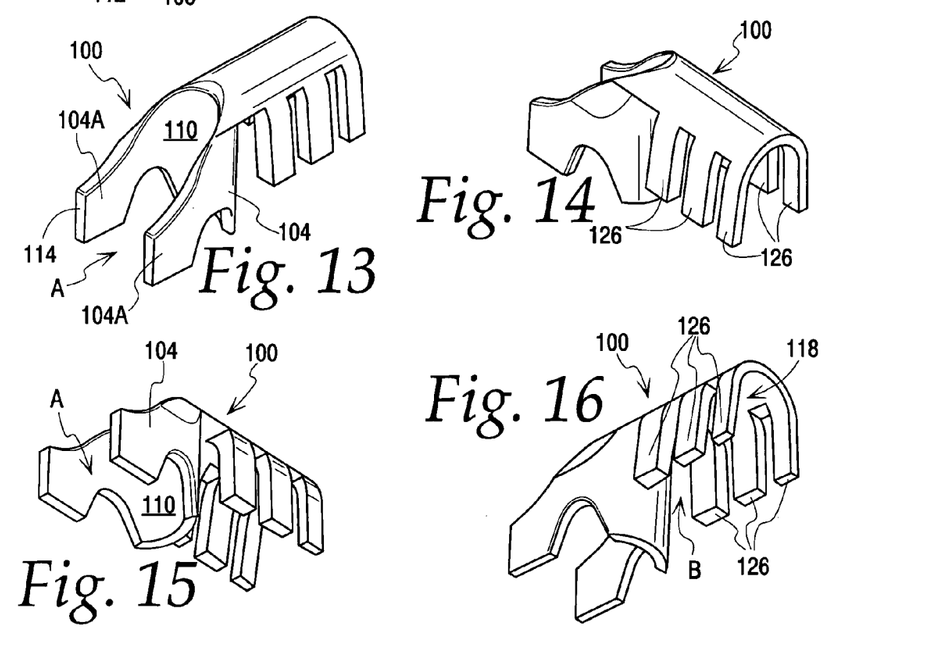
FIGS. 13-16 correspond to FIGS. 9-12, respectively, showing the ISJ prosthesis deformed for packaging and pre-implantation.

The prosthesis 40 is less likely to be displaced because it can be adjusted and/or crimped to the adjoined bones. Particularly, the elongate cavity 96 is adjustable for receiving a portion of the incus 24, as shown in FIG. 8. The elongate cavity 96 is adjustable owing to the malleability of the titanium. Also, the top slots 90, 92 and the elongate slot 88 allow the elongate cavity 96 to be adjusted to fit different diameters of the incus 24. Particularly, the side walls 68 and 70 can be deformed above the flanges 84 and 86 owing to use of the front slots 90, 92. Likewise, the side walls 68 and 70 can be moved closer together by collapsing the sides of the elongate slot 88. The spacer slots 80 and 82, the collar slot 62 and the keyhole slot 52 allow the tubular cavity 66 to be adjusted to fit the head 32 of the stapes 26.

As described, the size and shapes of the cavities 66 and 96 can be adjusted prior to or after placement on the stapes 26 and incus 24, as shown in FIG. 8. Additionally, the prosthesis 40 can be crimped to the bones of the incus 24 and stapes 26 using a forceps to tighten the connection. When the prosthesis is made from a shape memory material, the prostheses will be deformed by application of a signal such as heat after placement on the stapes and incus. The prosthesis 40 does not rely on compression between the malleus 22, the incus 24 and stapes 26 to hold the prosthesis in place until soft tissue encapsulation helps stabilize the prosthesis to adjoining bones. Nevertheless, growth of bone tissue will further stabilize the prosthesis 40 as the surface of the titanium body 42 may provide a scaffold for on growth.

Thus, in accordance with the one embodiment of the invention, there is provided an adjustable ISJ prosthesis.

FIGS. 9-12 illustrate an ISJ prosthesis 100 according to a second embodiment of the invention. The ISJ prosthesis 100 differs from the ISJ prosthesis 40, discussed above, in that its design is more particularly adapted for "self-crimping". The ISJ prosthesis 100 is manufactured of a unitary body of a shape memory material. The shape memory material may be a shape memory alloy, such as Nitinol, or a shape memory polymer, such as Calo-MER (The Polymer Technology Group, Berkeley, Calif.). With such a shape memory material, a portion of a prosthesis body can be deformed into an open configuration to provide spacing to allow the prosthesis to be placed over one or more bones, and when heat is applied to the prosthesis, the prosthesis self closes to lock around the bone structure.

Nitinol is a shape memory alloy that has proven biocompatibility. It can be manufactured via established means. The "memory" of the material is set while the material is in its martensitic phase. During this "shape setting operation" the in situ/final geometry of the prosthesis is established such that it will grasp the ossicle(s). After the shape setting operation, the geometry of the prosthesis is altered, i.e., deformed into the open configuration, in order to allow the prosthesis to be placed easily on the ossicle(s). This temporary or as shipped geometry is preferably maintained by packaging the prosthesis with a blocking member in the shape set cavity(s) such that the geometry change can not be initiated during storage or transit. Intraoperatively, a signal such as heat is applied in order to initiate the transformation of the prosthesis microstructure from martensite to austenite. This material phase transition causes the prosthesis to revert to its shape set "closed" and final geometry.

The user friendliness, functionality, and stability of several ossicular replacement devices can be improved by manufacturing them from a shape memory material. Examples of these devices include but are not limited to incudostapedial joints (ISJ) prosthetics, angular pistons, total ossicular replacement prostheses (TORPs) and partial ossicular replacement prostheses (PORPs).

The ISJ prosthesis 100 is preferably manufactured of a one piece deformable body 102 of a shape memory material. The body 102 comprises a generally cylindrical wall 104 having a generally planar bottom end 106 and an angled top end 108. The cylindrical wall 104 defines a generally tubular cavity 110 for receiving a head of a stapes. Rounded notches 112 are provided at opposite sides of the bottom end 106 for receiving the arches of a stapes. An elongate longitudinal slot 114 is provided at a front portion of the cylindrical wall 104 between the ends 106 and 108.

A second cylindrical wall 116 extends transversely from the first cylindrical wall 104 proximate the top end 108. The second cylindrical wall 116 defines an elongate cavity 118 for receiving an incus 24. A semi-cylindrical bridge 120 connects the second cylindrical wall 116 to the first cylindrical wall 104 at the top end 108. A pair of axially spaced transverse slots 122 are provided in the bottom half of the second cylindrical wall 116. A longitudinal slot 124 is provided at a lowermost part of the second cylindrical wall 116. The slots 122 and 124 define three fingers 126 on each of opposite sides of the longitudinal slot 124.

The ISJ prosthesis 100 is preferably formed by machining a single part. The ISJ prosthesis 100 is illustrated in both its machined condition and shape set condition in FIGS. 9-12. FIGS. 13-16 illustrate the ISJ prosthesis 100 deformed for packaging and implantation. Particularly, the first cylindrical wall 104 is opened at the slot 114 as shown at A to form arms 104A, to expose and enlarge the tubular cavity 100. Similarly, the fingers 126 are spread apart as shown at B to enlarge the elongate cavity 118 for packaging and implantation. Prior to surgery, the deformed ISJ prosthesis 110, see FIGS. 13-16, is placed so that the stapes head 32 is received in the opened tubular cavity 110 and the incus 24 is received in the opened elongate cavity 118. Intraoperatively, the shape memory of the ISJ prosthesis 100 is activated such that the fingers 126 close to grasp the incus and the arms 104A grab the stapes head by returning to the position shown in FIGS. 9-12, thereby reconnecting the incus to the stapes and allowing for the transmission of sound vibration through the ossicles to the structures of the inner ear.

Figure 17:
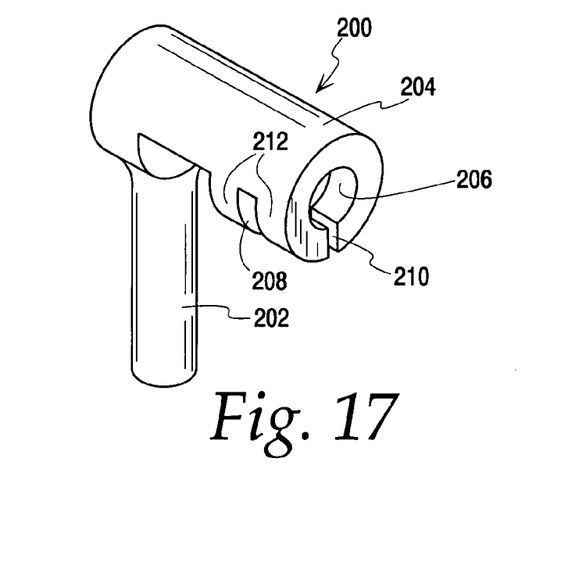
FIG. 17 is an upper rear perspective view of an angular piston prosthesis in accordance with the invention.

FIG. 17 illustrates a middle ear prosthesis in the form of an angular piston 200. The angular piston 200 is formed of a unitary body of a shape memory material. The angular piston 200 comprises an elongate rod or piston 202. Extending transversely from the piston 202 is a cylindrical wall 204 defining an elongate cavity 206. The cylindrical wall 204 is generally similar to the second cylindrical wall 116, discussed above relative to the ISJ prosthesis 100. In the illustrated embodiment, the cylindrical wall 204 includes a single slot 208 transverse to the axis and a longitudinal slot 210 to define opposite arms 212 on either side.

The angular piston 200 is shown in the machined and shaped set form. The arms 212 can be deformed, similar to that discussed above relative to the ISJ prosthesis 100, for implantation. The angular piston 200 is used to replace the stapes. The incus is captured in the elongate cavity 206 and the piston or rod 202 is received in a hole in the foot plate or oval window, as is well known. Intraoperatively, the shape memory property of the angular piston 200 is activated, such as by heat, so that the arms 212 grasp the incus to allow for transmission of sound vibration through the ossicles to the structures of the inner ear. As will be apparent, the rod 202 could be of a different material than the cylindrical wall 204 and the components be secured together by any known means. It is also appreciated that a straight stapes piston can be constructed in a similar manner, such as the slotted bucket stapes prostheses described in U.S. Ser. No. 11/428,672 and U.S. Pat. No. 7,087,081, both incorporated by reference herein, wherein the slotted bucket can be made from malleable or shape memory materials.

Figure 18:
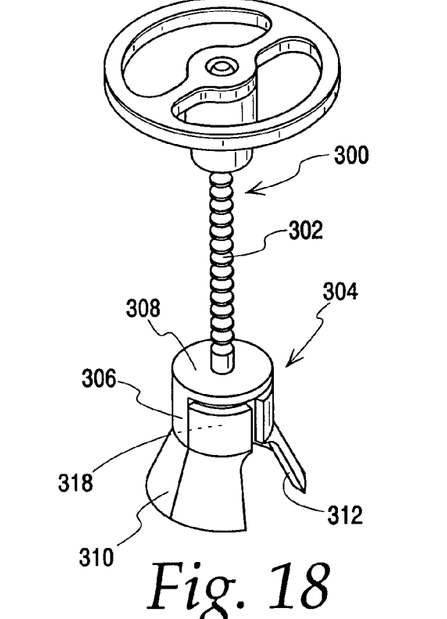
FIGS. 18 and 19 are perspective views of an ossicular replacement prosthesis with a cup portion shown as machined.
Figure 19:
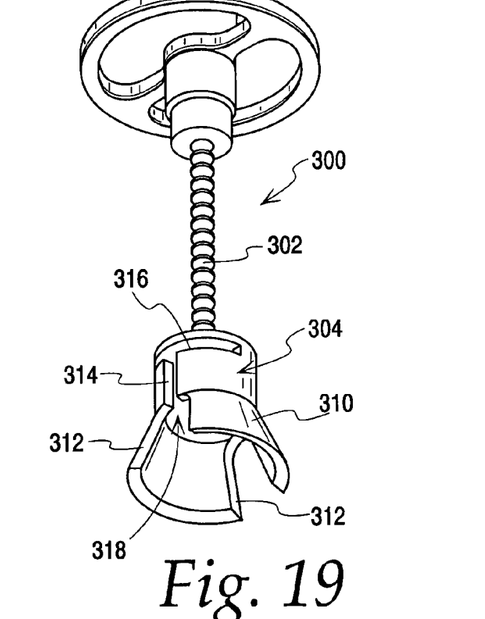

Shape memory materials can also be used to manufacture total ossicular replacement prostheses (TORPs) and partial ossicular replacement prostheses (PORPs). FIGS. 18 and 19 illustrate an adjustable length PORP prosthesis 300. The prosthesis 300 permits length adjustment using structure generally similar to that described in U.S. Pat. No. 6,168,625, owned by the assignee of the present application, and the specification of which is hereby incorporated by reference herein.

Figure 20:
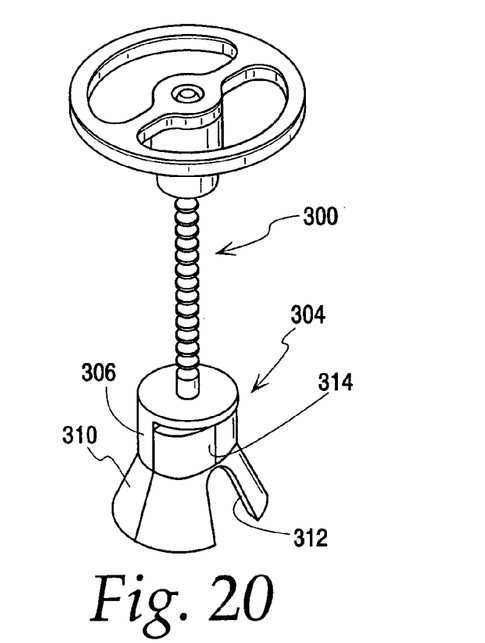
FIG. 20 is a perspective view similar to FIG. 18 showing the cup in a shape set position.
Figure 21:
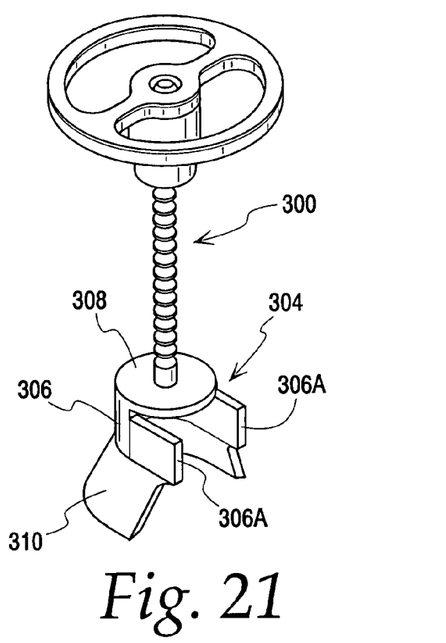
FIG. 21 is a perspective view similar to that of FIGS. 18 and 20, showing the cup in an open position for packaging and pre-implantation.

The prosthesis 300 has a head 301 longitudinally displaceable on a shaft 302, as in the '625 patent. A "cup" 304 formed of a shape memory material is connected to the shaft 302, opposite the head 301. The cup 304 comprises a cylindrical wall 306 closed by a top wall 308 at one end and connecting to a conical wall 310 at a lower end. Preferably rounded notches 312 are provided in diametrically opposite sides of the conical wall 312. The cylindrical wall 306 includes a longitudinal slot 314 opening into one of the rounded notches 32. A transverse slot 316 perpendicular to the longitudinal slot 314 is provided just below the top wall 308. The cylindrical wall 306 defines a tubular cavity 318 for receiving the head or capitulum of a stapes. The adjustable length prosthesis 300 is illustrated with the cup 304 in the machined or closed configuration in FIGS. 18 and 19. FIG. 20 illustrates the cup 304 in the shape set position, described below. FIG. 21 illustrates the adjustable length prosthesis 300 deformed for packaging. The cup 304 is opened by spreading the cup 304 apart at the slot 314 to form arms 306A. The length of the prosthesis 300 can then be adjusted by moving the head 301 along the shaft 302 and removing the portion of the shaft that extends beyond the head. The opened cup 304, see FIG. 21, is positioned over the head of the stapes. The shape memory material is activated such that the cup 304 returns to the closed shape set position shown in FIG. 20, with the arms 306A closing to grasp or otherwise retain the stapes head thereby reconnecting the stapes to the ear drum for transmission of sound vibration to the structures of the inner ear.

Figure 22:
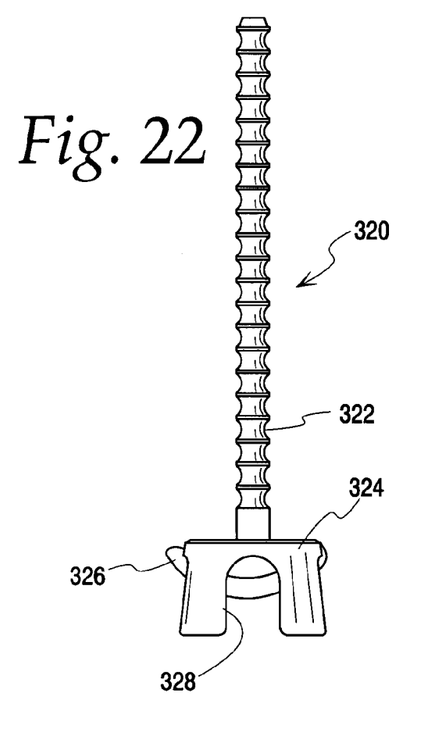
FIG. 22 is a side elevation view of a partial ossicular replacement prosthesis with a locking arm in a set position.
Figure 23:
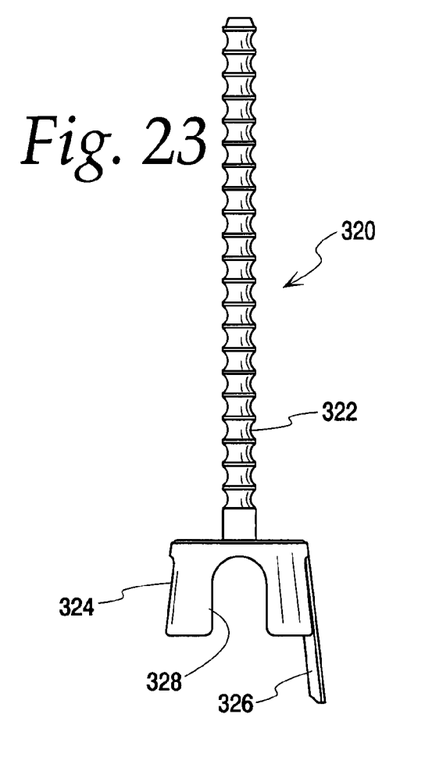
FIG. 23 is an elevation view similar to FIG. 22 showing the locking arm in the open position for packaging and pre-implantation.

FIG. 22 illustrates an adjustable length prosthesis 320, similar to the prosthesis 300 of FIG. 18, with the head removed, according to an alternative embodiment of the invention. In this embodiment, the prosthesis 320 includes a shaft 322 and a cup 324. The cup does not open as in the embodiment 304, above. Instead, a tab 326 is provided for locking the arch of a stapes when received in rounded notches 328. The tab 326 is shown in the shape set position in FIG. 22. FIG. 23 illustrates the tab 326 deformed for packaging. During the operation, the stapes head is received in the cup 324, with the arches resting in the notches 328. The shaped memory material is heat activated such that the tab 326 returns to the position of FIG. 22, extends through the stapes arch and under the capitulum of the stapes dead to grasp and retain the stapes.

There have been described and illustrated herein several embodiments of ossicular prostheses. While particular embodiments of the invention have been described, including ISJs, angular pistons, and PORPs, it is not intended that the invention be limited thereto, as it is intended that the invention be as broad in scope as the art will allow and that the specification be read likewise. Thus, while particular specific shape memory materials have been disclosed, it will be appreciated that other suitable shape memory materials, both metallic and polymeric can be used as well. In addition, slots have been disclosed so as to define structure which can deform in accord with the invention, it is appreciated that the term 'slot' or 'slots', while including the shown straight linear voids, should not be limited to voids between elements which have straight or parallel opposing sides. As such, a slot may be defined by structure having one or more curvilinear sides, or the slot may be defined by material having sides obliquely angled relative to each other. The essence of slot, for purposes of the application, is a narrow void separating two structural elements such that in view of such void, at least one of the structural elements can be deformed relative to the other into an open position to facilitate access to an anatomical structure and/or into a closed position to retain an anatomical structure. While several exemplar embodiments including such structural elements and slot(s) have been described, it is appreciated that other embodiments may be constructed as well. Furthermore, while machining is described for manufacturing several embodiments, it is recognized that such machining may be via any suitable process including laser cutting, EDM, drills and blades, etc. Also, the prostheses, and individual portions thereof, may be made by means other than or in addition to machining, including molding. It will therefore be appreciated by those skilled in the art that yet other modifications could be made to the provided invention without deviating from its scope as claimed.

We claim:

1. A middle ear prosthesis comprising:
   a unitary body of deformable shape memory material capable of retaining different shapes, the body comprising a wall at least partially defining a cavity for receiving a bone of the middle ear, the wall including at least one slot and being deformable proximate said at least one slot between an open position for receiving the bone and a closed position, wherein the body is reshaped to grasp the bone, wherein the body comprises a second slotted wall defining a second cavity generally perpendicular to the first cavity to define an incudo-stapedial joint prosthesis.

2. The middle ear prosthesis of claim 1 wherein the body is of Nitinol.

3. The middle ear prosthesis of claim 1 wherein the body is of a shape memory polymer.

4. A middle ear prosthesis comprising:
a unitary body of deformable shape memory material capable of retaining different shapes, the body comprising a wall at least partially defining a cavity for receiving a bone of the middle ear, the wall including at least one slot and being deformable proximate said at least one slot between an open position for receiving the bone and a closed position, wherein the body is reshaped to grasp the bone, further comprising a rod coupled to the body and angled relative to cavity to define an angular piston.

5. The middle ear prosthesis of claim 4 wherein the body is of Nitinol.

6. The middle ear prosthesis of claim 4 wherein the body is of a shape memory polymer.

7. A middle ear prosthesis comprising:
a unitary body formed from one piece of deformable shape memory material capable of retaining different shapes, the body comprising a generally tubular cavity for receiving a head of a stapes and an elongate cavity extending generally perpendicular to the generally tubular cavity for receiving an incus, wherein the body can be reshaped responsive to an external signal to fit the stapes and the incus.

8. The middle ear prosthesis of claim 7 wherein the body comprises a collar defining the generally tubular cavity, the collar having a longitudinally extending through slot.

9. The middle ear prosthesis of claim 7 wherein the body comprises a generally semi-cylindrical wall connected to opposite parallel walls having inwardly extending flanges defining the elongate cavity.

10. The middle ear prosthesis of claim 9 wherein the opposite parallel walls are connected to the semi-cylindrical wall by bridges to define elongate slots between the opposite parallel walls and the semi-cylindrical wall.

11. The middle ear prosthesis of claim 10 wherein the flanges are spaced apart to define a cavity slot.

12. The middle ear prosthesis of claim 7 wherein the body comprises a generally cylindrical slotted wall defining the elongate cavity.

13. The middle ear prosthesis of claim 7 wherein the body is of Nitinol.

14. An incudo-stapedial joint prosthesis comprising:
a deformable unitary body of shape memory material comprising a generally tubular first wall defining a first cavity for receiving a head of a stapes and a second wall connected to the first wall defining a second cavity extending generally perpendicular to the first cavity for receiving an incus, each of said first and second walls including at least one slot, wherein the body can be reshaped intraoperatively in response to an external signal relative to said at least one slot in said first wall and said at least one slot in said second wall to fit the stapes and the incus.

15. The incudo-stapedial joint prosthesis of claim 14 wherein the body is of Nitinol.

16. An incudo-stapedial joint prosthesis comprising:
a unitary body of shape memory material comprising a generally tubular wall defining a first cavity for receiving a head of a stapes and a generally U-shaped wall connected to the tubular wall defining a second cavity extending generally perpendicular to the first cavity for receiving an incus, the tubular wall comprising at least one slot to enable the first cavity to be sized to fit the head of the stapes and the generally U-shaped wall comprising at least one slot to enable the second cavity to be sized to fit the incus.

17. The incudo-stapedial joint prosthesis of claim 16 wherein the body comprises a generally semi-cylindrical wall connected to opposite parallel walls to define the generally U-shaped wall and connected to arcuate wall portions longitudinally spaced from the opposite parallel walls by spacer slots to define the generally tubular wall.

18. A shape memory incudo-stapedial joint prosthesis comprising:
a body of shape memory material comprising a generally tubular wall defining a first cavity for receiving a head of a stapes and a generally cylindrical wall connected to the tubular wall defining a second cavity extending generally perpendicular to the first cavity for receiving an incus, the tubular wall comprising slots to enable the first cavity to be deformed preoperatively and the generally cylindrical wall comprising slots to enable the second cavity to be deformed preoperatively, wherein the body can be activated intraoperatively so that the cavities return to a shape memory position wherein the first cavity grasps the head of the stapes and the second cavity grasps the incus.

19. The shape memory incudo-stapedial joint prosthesis of claim 18 wherein the body is of Nitinol.

20. An incudo-stapedial joint prosthesis, comprising:
a unitary body of shape memory material defining first and second cavities, the first cavity having a first axis and sized to receive the head of the stapes and the second cavity sized for receiving a portion of the incus and having a second axis angled relative to the first axis, the body about at least one of the first and second cavities including at least one slot at which the respective cavity can be deformed into an open position and wherein the body can be activated intraoperatively to assume a shape memory position in which the respective cavity including the at least one slot grasps a portion of an ossicle.

21. An incudo-stapedial joint prosthesis according to claim 20, wherein the body is of Nitinol.

* * * * *